(12) United States Patent
Unvert et al.

(10) Patent No.: US 7,001,414 B2
(45) Date of Patent: Feb. 21, 2006

(54) LEG TANNING APPARATUS

(75) Inventors: David Unvert, Bonita, CA (US); Patryk Reczek, Westlake, CA (US)

(73) Assignee: Classic Legs, Inc., Bonita, CA (US)

( * ) Notice: Subject to any disclaimer, the term of this patent is extended or adjusted under 35 U.S.C. 154(b) by 67 days.

(21) Appl. No.: 10/278,874

(22) Filed: Oct. 23, 2002

(65) Prior Publication Data

US 2003/0060853 A1 Mar. 27, 2003

Related U.S. Application Data

(60) Provisional application No. 60/335,882, filed on Oct. 23, 2001.

(51) Int. Cl.
*A61B 5/06* (2006.01)

(52) U.S. Cl. .............. 607/91; 607/88; 607/90; 606/9

(58) Field of Classification Search ........... 607/88–95; 606/9, 10
See application file for complete search history.

(56) References Cited

U.S. PATENT DOCUMENTS

| | | | | |
|---|---|---|---|---|
| 4,177,384 A | * | 12/1979 | Wolff | 250/494.1 |
| 4,835,400 A | | 5/1989 | Wolff | 250/504 |
| 4,846,525 A | | 7/1989 | Manning | 297/180 |
| 5,086,769 A | | 2/1992 | Vianello et al. | 128/377 |
| 5,087,095 A | | 2/1992 | McFate | 297/129 |
| 5,466,248 A | * | 11/1995 | Whitson-Newman | 607/88 |
| 5,902,327 A | * | 5/1999 | Scott et al. | 607/90 |
| 5,947,561 A | | 9/1999 | Ryan | 297/391 |
| 5,975,630 A | | 11/1999 | Schreiber | 297/217.3 |
| 6,273,906 B1 | * | 8/2001 | Swanson | 607/91 |
| 6,443,978 B1 | * | 9/2002 | Zharov | 607/91 |
| 6,461,376 B1 | * | 10/2002 | Beshore | 607/91 |
| 2004/0098071 A1 | * | 5/2004 | Chapman et al. | 607/94 |

OTHER PUBLICATIONS

SunCo Distributors "HL 38 Classic Legs" Leg Tanner brochure, http://www.suncotan.com/html/equipment/leg_tanner.html.*

Sun Power Source "Classic aleg Tanner", http://sunpowersource.com/Merchant2/merchant.mv?Screen=PROD&Store_Code=SPS&Product_Code=CL-LT&Category_Code=Itan.*

Tan & Float "HL 38 Classic Leg Tanner," http://www.tanandfloat.co.uk/legtan.html.*

Wolf Tanning Systems "LegacyTM" leg tanner brochure, see Appendix B.*

* cited by examiner

*Primary Examiner*—A. Farah
(74) *Attorney, Agent, or Firm*—Patterson, Thuente, Skaar & Christensen, P.A.

(57) ABSTRACT

A leg tanning apparatus including a tanning module and a support module. The tanning module has a length that is on the order of a length of legs on a human body. The tanning module includes an outer shell and a plurality of tanning bulbs that are mounted in the outer shell. The plurality of bulbs are capable of emitting ultraviolet light. The support module maintains the tanning module at an acute angle.

20 Claims, 4 Drawing Sheets

LEG TANNING APPARATUS

REFERENCE TO RELATED APPLICATION

This application claims priority to U.S. Provisional Application Ser. No. 60/335,882, filed Oct. 23, 2001.

FIELD OF THE INVENTION

The present invention relates generally to an apparatus for tanning at least a portion of the skin of a human body. More particularly, the present invention relates to an apparatus for tanning legs on a human body.

BACKGROUND OF THE INVENTION

Tanning beds that produce ultraviolet light are very popular, as they permit persons to obtain a tan when the ambient conditions or the persons' schedules do not enable the persons to obtain a natural tan such as by laying in the sun. For example, in northern climates, the portion of the year in which a person can obtain a natural tan is quite limited.

Additionally, it is often difficult to monitor the tanning process when laying in the sun. When the person gets more than a specified amount of exposure, the person experiences sun burn, which not only causes the person discomfort but also damages the skin.

Tanning beds typically have an upper tanning unit and a lower tanning unit connected by hinges so that the upper unit can be opened and closed in a manner analogous to a clamshell. The upper tanning unit and the lower tanning unit each have a plurality of tanning bulbs mounted therein. These tanning bulbs are fabricated to emit advantageous concentrations of ultraviolet rays that effect tanning of the skin on the user's body.

When in the open position, a person can enter the apparatus to lie down on the lower tanning unit. The upper tanning unit is then closed to form an internal tanning chamber where the person is substantially surrounded by tanning lamps. Tanning bulbs used in these tanning units extend substantially from the user's head to the user's feet to effect tanning of substantially all the exposed skin on the user's body.

In another configuration, the tanning unit is configured to tan the user's skin as the user is standing. This type of tanning unit is particularly popular with persons who feel uncomfortable when laying in an enclosed horizontally oriented tanning unit. Similar to the horizontally oriented tanning units, this so-called stand-up unit effects tanning of substantially all of the exposed skin on the user's body.

SUMMARY OF THE INVENTION

The present invention is directed to a leg tanning apparatus that includes a tanning module and a support module. The tanning module has a length that conforms with a length of legs on a human body.

The tanning module includes an outer enclosure and a plurality of tanning bulbs. The outer enclosure has a recess formed therein. The plurality of tanning bulbs are mounted in the outer enclosure. The plurality of bulbs are capable of emitting ultraviolet light. The support module maintains the tanning module at an acute angle.

DETAILED DESCRIPTION OF THE PREFERRED EMBODIMENTS

Figure 1:
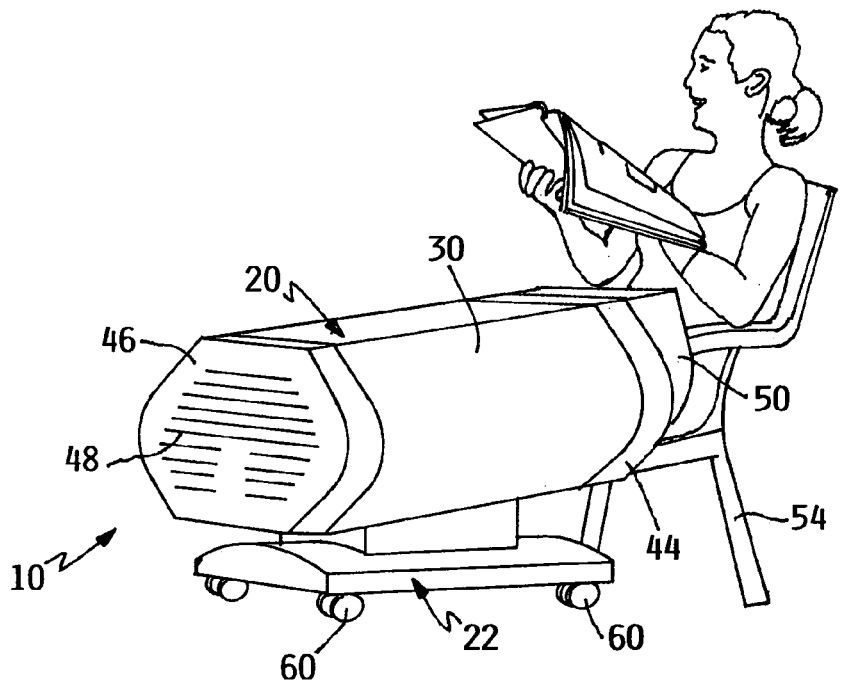
FIG. 1 is a perspective view of a leg tanning apparatus of the present invention.

An embodiment of the present invention is directed to a leg tanning apparatus, as most clearly illustrated in FIGS. 1–6. The leg tanning apparatus 10 is particularly suited for tanning a person's legs.

Certain individuals desire to tan the skin on selected parts of the body as opposed to tanning the entire skin on the body. For example, during particular activities, it is desirable for the skin on the person's legs to be tan. The leg tanning apparatus 10 of the present invention enables persons to effect tanning of the user's legs. Another benefit of just tanning a person's legs is that many people find that it is more difficult to obtain a desired level of tanning on their legs than on other portions of the body.

The leg tanning apparatus 10 generally includes a tanning module 20 that is mounted with respect to a support module 22. The tanning module 20 has a length of between 2 feet and 5 feet. The tanning module 20 has an outer shell 30, as most clearly illustrated in FIGS. 3 and 4. The outer shell 30 includes a recess 33 formed therein. A plurality of tanning bulbs 32 is attached to the outer shell 30 in the recess 33.

While the outer shell 30 is illustrated as being of a one-part configuration, a person of ordinary skill in the art will appreciate that it is possible to form the outer shell 30 with upper and lower sections that are pivotally attached so that the outer shell 30 is movable between an open configuration and a closed configuration. Even though it is preferable for the tanning bulbs 32 to extend around the user's legs, it is also possible to use alternate configurations where the tanning bulbs do not substantially extend around the user's legs.

The tanning bulbs 32 are arranged to extend around the outer shell 30 in a spaced-apart relationship. A person of ordinary skill in the art will appreciate that it is possible to select tanning bulbs 32 that emit particular concentrations of light in the UV-A and UV-B wavelengths to produce desired tanning results.

The leg tanning apparatus 10 preferably includes 38 tanning bulbs 32. A person of ordinary skill in the art will appreciate that the number of tanning bulbs 32 and the spacing between the tanning bulbs 32 is selected based upon a variety of factors such as the wattage of the tanning bulbs 32 and the ultraviolet emission characteristics of the tanning bulbs 32.

The tanning bulbs 32 have a length of less than 4 feet, preferably between 2 feet and 4 feet, and most preferably about 3 feet. The tanning bulbs 32 have an output of less than 150 watts, preferably between 40 watts and 100 watts, and most preferably about 65 watts. A person of ordinary skill in the art will appreciate that it is possible to adapt the concepts of the present invention for use with different types of tanning bulbs, such as so-called high-pressure tanning bulbs.

Figure 4:
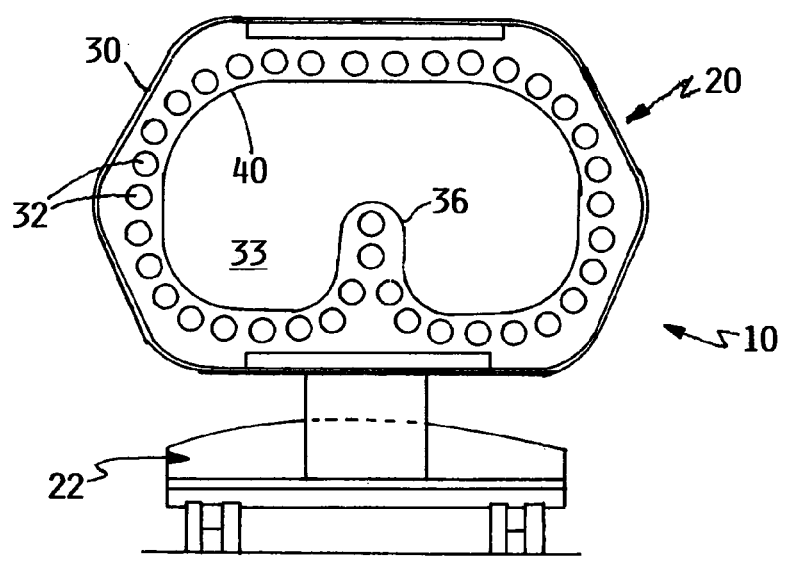
FIG. 4 is a front sectional view of the leg tanning apparatus.
Figure 5:
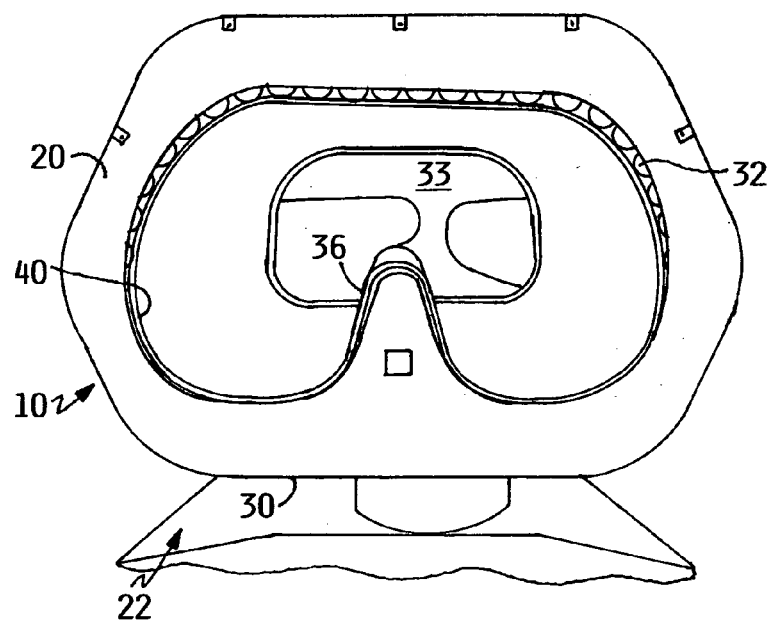
FIG. 5 is a front view of the leg tanning apparatus with an end cover removed.
Figure 6:
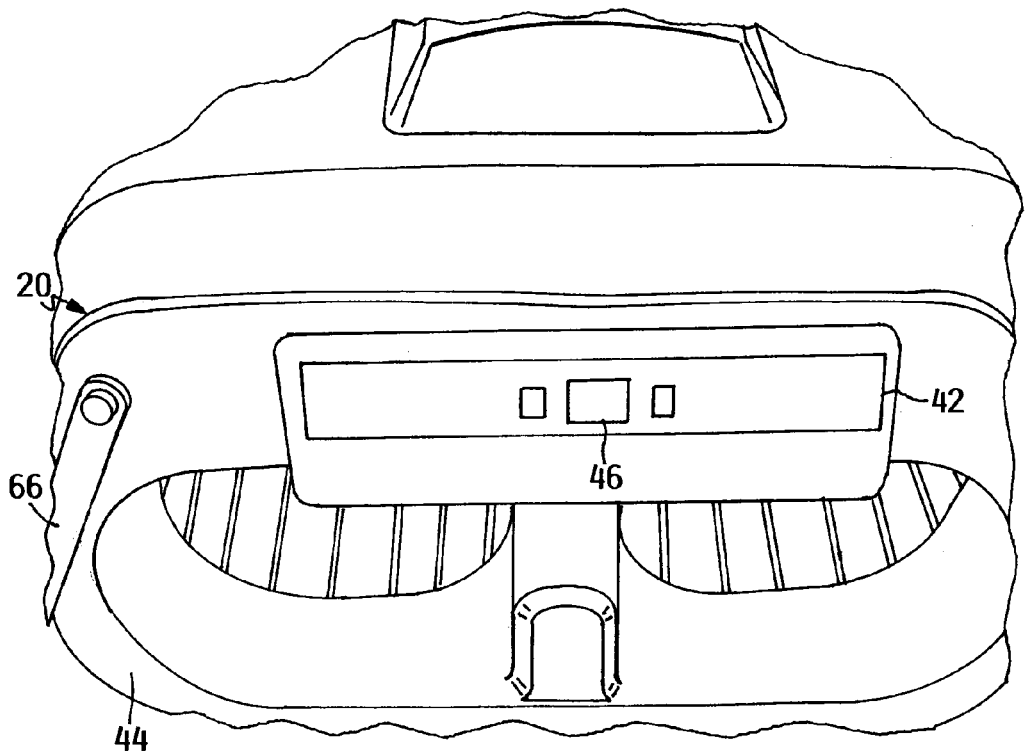
FIG. 6 is a close-up view of a control panel on the leg tanning apparatus.
Figure 7:
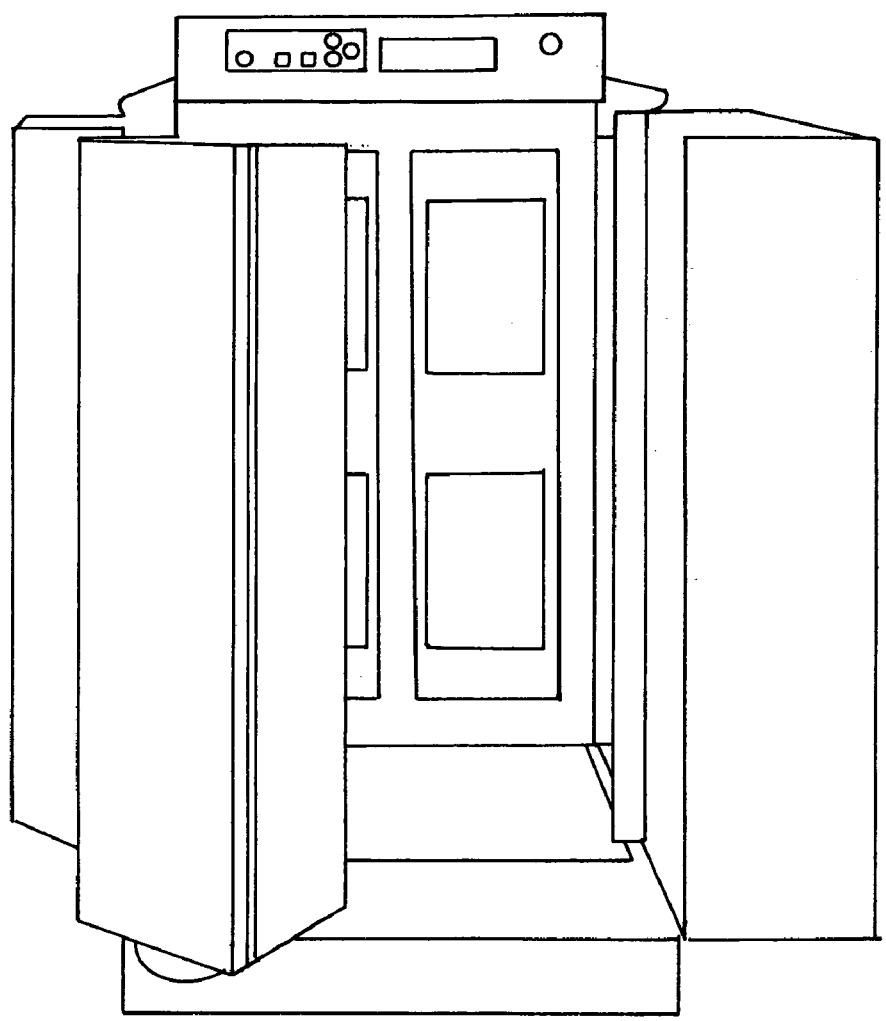
FIG. 7 is a side view of a prior art leg tanning apparatus.

The tanning module 20 preferably includes an upwardly extending central section 36, as most clearly illustrated in FIGS. 4 and 5. The upwardly extending central section 36 enhances the ability to effect tanning of the skin on the inner portions of the user's legs. A person of ordinary skill in the art will appreciate that the central section 36 may also extend downwardly from the top of the tanning module 20.

A protective layer 40 is preferably placed over the tanning bulbs 32 to prevent the person's legs from directly contacting the tanning bulbs 32. The protective layer 40 is preferably a clear acrylic sheet that is shaped to substantially conform to the inner surfaces of the tanning bulbs 32.

A control panel 42 is preferably mounted on a front end 44 of the tanning module 20. The control panel 42 enables the tanning module 20 to be turned on and off. The control panel 42 also preferably provides a timer 46, which enables a person using the leg tanning apparatus 10 to see how much time is remaining in a tanning session.

A shield 50 is preferably attached to the front end 44 of the tanning module 20. The shield 50 lays against the person's body to substantially prevent ultraviolet radiation from escaping through the front end 44.

The shield 50 thereby obviates the need of the person using the leg tanning apparatus 10 from having to use eye protection while using the leg tanning apparatus 10. The shield 50 thereby permits the person using the leg tanning apparatus 10 to do other activities, like read a book, when the leg tanning apparatus 10 is operating.

A back end 46 of the tanning module 20 preferably includes a fan 48, as illustrated in FIG. 1, which pulls air through the tanning module 20. The fan 48 thereby enhances the comfort of the person using the leg tanning apparatus 10. A control for the fan 48 is preferably provided on the control panel 42.

Figure 2:
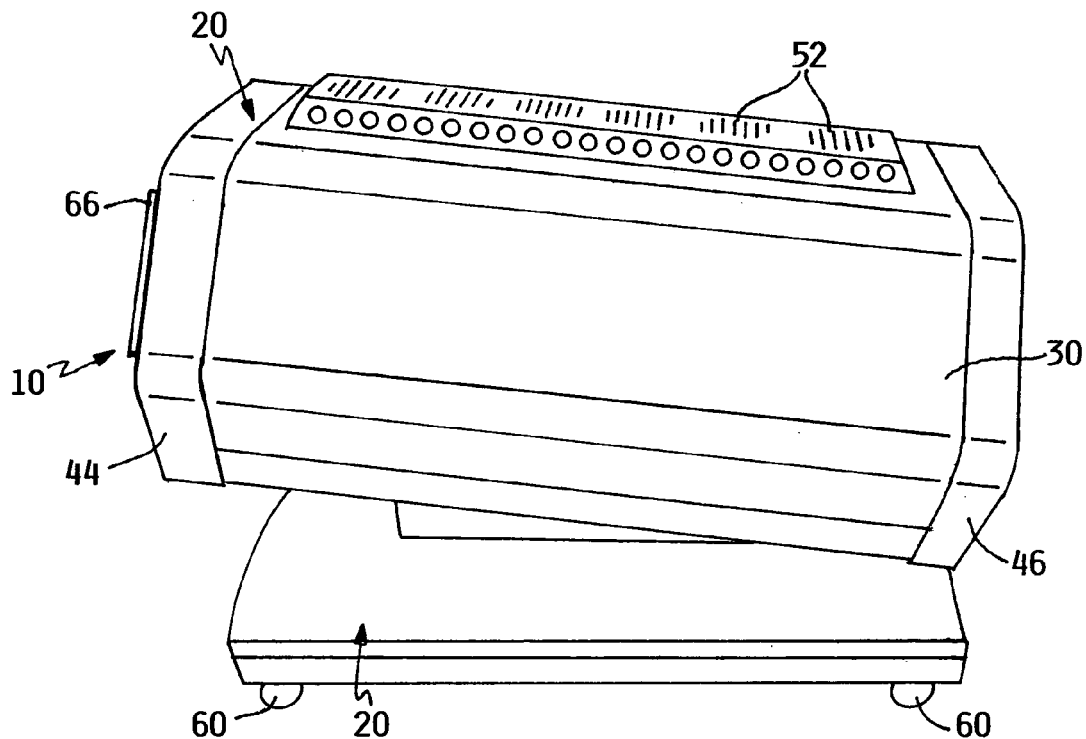
FIG. 2 is side view of the leg tanning apparatus.
Figure 3:
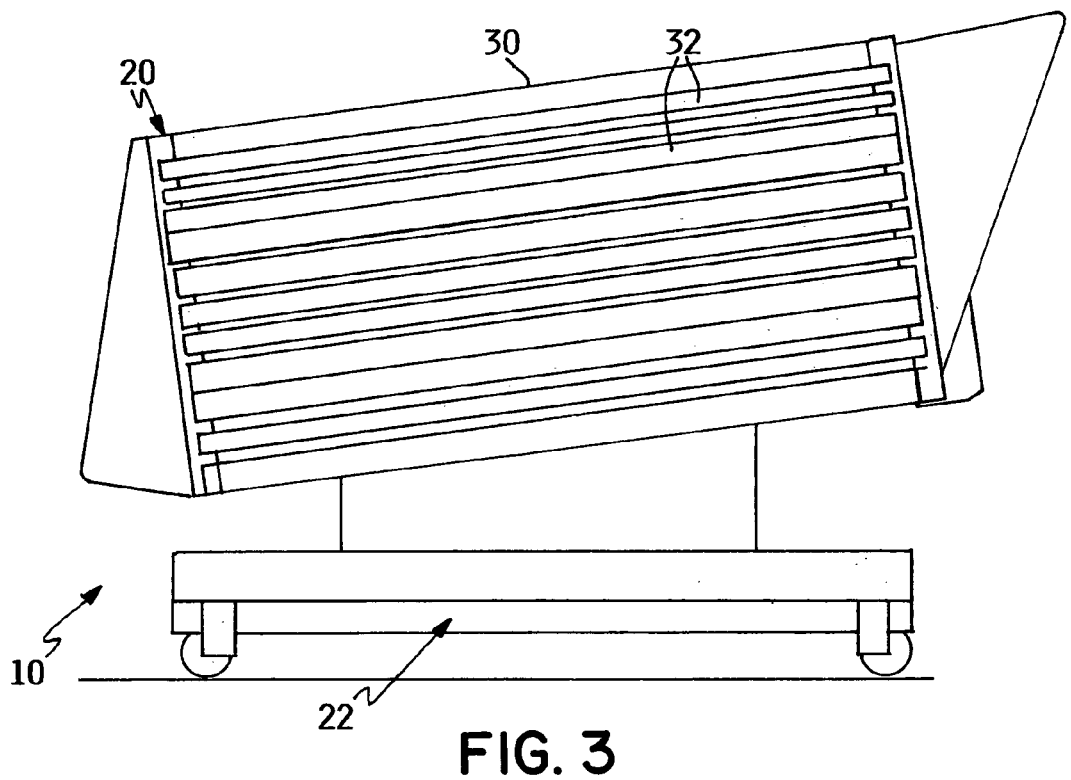
FIG. 3 is a side sectional view of the leg tanning apparatus.

The tanning module 20 may also include a plurality of fans 52 that are mounted on the top of the outer shell 30, as illustrated in FIG. 2. The fans 52 facilitate cooling of the internal portions of the leg tanning apparatus 10.

The support module 22 maintains the tanning module 20 at a desired position to facilitate using the leg tanning apparatus 10 while a person is sitting in a conventional chair 52. The support module 22 preferably positions the front end 44 slightly higher than the back end 46 to facilitate the comfort of the user. The support module 22 orients the tanning module 20 at an acute angle. The angle is less than 45°, preferably between about 0° and 25°, and most preferably about 10°.

The support module 22 may also include the ability to change the orientation of the tanning module 20 to enhance the flexibility of the leg tanning apparatus 10. A person of ordinary skill in the art will appreciate that gas-filled struts may be used to maintain the tanning module 20 at a desired angular orientation.

The support module 22 preferably includes a plurality of wheels 60 mounted thereto. The wheels 60 facilitate pulling the leg tanning apparatus 10 towards the chair 54 where the person is sitting. Alternatively, the chair 54 may be mounted on wheels (not shown) to facilitate moving the chair 54 towards the leg tanning apparatus 10.

When the wheels 60 are mounted on the support module 22, the leg tanning apparatus 10 preferably includes at least one handle 66 mounted proximate the front end 44 to facilitate moving the leg tanning apparatus 10.

Depending on the type of tanning bulbs 32 used in the leg tanning apparatus 10, it may be necessary to use ballasts (not shown) to appropriately power the tanning bulbs 32. The ballasts are preferably mounted in the support module 22. The number and size of ballasts is selected based upon the type of tanning bulbs 32. Preferably, the ballasts are 80-watt ballasts, which are underpowered.

When ballasts are mounted in the support module 22, at least one cooling fan (not shown) is preferably provided in the support module 22 to maintain the support module 22 within a desired operating temperature. A person of ordinary skill in the art will appreciate that the number and size of the cooling fans is selected based upon the number and size of the ballasts.

In operation, the person sits on the chair 54 and extends his/her legs into the tanning module 20. The person then pulls the leg tanning apparatus 10 towards the chair 54 so that substantially all of the person's legs are in the tanning module 20. Next, the leg tanning apparatus 10 is activated to effect tanning of the person's legs. Once the session is completed, the person pushes the leg tanning apparatus 10 away from the chair 54 to remove the legs from the tanning module 20.

Another aspect of the present invention relates to a tanning bed in which tanning bulbs extend substantially from a user's feet to a user's head to effect tanning of substantially all of the exposed skin on the user's body where the tanning bed further includes an upwardly extending central section. The upwardly extending central section preferably has a length that is less than the tanning bed and is positioned proximate the user's legs. The upwardly extending central section enhances the ability to effect tanning of the skin on the inner portions of the user's legs. A person of ordinary skill in the art will appreciate that the central section may also extend downwardly from the top of the tanning bed.

It is contemplated that features disclosed in this application, as well as those described in the above applications incorporated by reference, can be mixed and matched to suit particular circumstances. Various other modifications and changes will be apparent to those of ordinary skill.

What is claimed is:

1. A leg tanning apparatus comprising:
   a tanning module having a length that is on the order of a length of legs on a human body,
   the tanning module comprising:
   an outer shell defining an enclosed interior space; and
   a plurality of tanning bulbs mounted to the outer shell, wherein the plurality of bulbs are capable of emitting ultraviolet light; and
   a support module maintaining the tanning module at an angle of more than 0° and less than 45° so that a front end of the tanning module is positioned higher than a back end of the tanning module.

2. The leg tanning apparatus of claim 1, and further comprising a central section that extends inwardly from the outer shell, wherein at least one of the plurality of tanning bulbs is located in the central section.

3. The leg tanning apparatus of claim 1, and further comprising a protective layer that extends over substantially all of the plurality of tanning bulbs.

4. The leg tanning apparatus of claim 1, wherein the tanning module and the support module are formed in a single unit.

5. The leg tanning apparatus of claim 1, and further comprising a plurality of wheels operably attached to the support module.

6. The leg tanning apparatus of claim 1, wherein the angle is adjustable.

7. The leg tanning apparatus of claim 1, wherein the tanning module has a length of between about 2 feet and 5 feet.

8. A system for tanning legs of a human body comprising:
a leg tanning apparatus comprising:
  a tanning module having a length of less than about 5 feet, the tanning module comprising:
    an outer shell; defining an enclosed interior space and
    a plurality of tanning bulbs mounted to the outer shell, wherein the plurality of bulbs are capable of emitting ultraviolet light; and
  a support module maintaining the tanning module at an angle of more than 0° and less than 45° so that a front end of the tanning module is positioned higher than a back end of the tanning module; and
a chair having a seating surface that is elevated above a ground surface, wherein the chair enables a person to sit while the person extends his/her legs into the leg tanning apparatus to effect tanning of the skin on the person's legs with ultraviolet radiation.

9. The system of claim 8, and further comprising a central section that extends inwardly from the outer shell, wherein at least one of the plurality of tanning bulbs is located in the central section.

10. The system of claim 8, and further comprising a protective layer that extends over substantially all of the plurality of tanning bulbs.

11. The system of claim 8, wherein the tanning module and the support module are formed in a single unit.

12. The system of claim 8, and further comprising a plurality of wheels operably attached to the support module.

13. The system of claim 8, wherein the angle is adjustable.

14. The system of claim 8, wherein the tanning module has a length of between about 2 feet and 5 feet.

15. A leg tanning apparatus comprising:
an outer shell defining an enclosed interior space;
a plurality of tanning bulbs mounted to the outer shell, wherein the plurality of bulbs are capable of emitting ultraviolet light; and
a central section that extends inwardly from the outer shell, wherein at least one of the plurality of tanning bulbs is located in the central section.

16. A method of tanning legs of a human body comprising:
providing a leg tanning apparatus comprising an outer shell defining an enclosed interior space and a plurality of tanning bulbs that are capable of emitting ultraviolet radiation;
mounting the leg tanning apparatus at an angle of more than 0° and less than 45° with respect to a ground surface so that a front end of the leg tanning apparatus is positioned higher than a back end of the leg tanning apparatus;
extending a person's legs into the leg tanning apparatus; and
emitting ultraviolet radiation from the plurality of tanning bulbs, wherein the ultraviolet radiation effects tanning of skin on the legs.

17. The method of claim 16, and further comprising forming a central section that extends inwardly from the outer shell, wherein at least one of the plurality of tanning bulbs is located in the central section.

18. The method of claim 16, and further comprising providing a protective layer that extends over substantially all of the plurality of tanning bulbs.

19. The method of claim 16, wherein the angle is adjustable.

20. The method of claim 16, wherein the tanning module has a length of between about 2 feet and 5 feet.

\* \* \* \* \*